United States Patent [19]

Nappa

[11] Patent Number: 5,283,382
[45] Date of Patent: Feb. 1, 1994

[54] FLUORINATION PROCESS

[75] Inventor: Mario J. Nappa, Newark, Del.

[73] Assignee: E. I. du Pont de Nemours and Company, Wilmington, Del.

[21] Appl. No.: 965,550

[22] Filed: Oct. 23, 1992

Related U.S. Application Data

[63] Continuation of Ser. No. 810,525, Dec. 18, 1991, abandoned, which is a continuation of Ser. No. 532,617, Jun. 4, 1990, abandoned.

[51] Int. Cl.$^5$ .............................................. C07C 17/08
[52] U.S. Cl. ..................................... 570/168; 570/169
[58] Field of Search ............................. 570/168, 169

[56]     References Cited
U.S. PATENT DOCUMENTS
4,258,225   3/1981   Feiring ............................. 570/168

FOREIGN PATENT DOCUMENTS
0256146   2/1988   European Pat. Off. .

OTHER PUBLICATIONS

Pavlath, A. E., "Aromatic Fluorine Compounds", p. 45, OD412.F1P3 (1962).
Barbour, A. K., "Advances in Fluorine Chemistry", p. 184, vol. 3, QD181.F1A33V.3 (1963).
Feiring, A. E., "Chemistry in Hydrogen Fluoride v. Catalysts for Reaction of HF with Halogenated Olefins", pp. 7-18, 13(1979).
Feiring, A. E., Journal of Fluorine Chemistry, 13, 7-18 (1979).
Cotton Advanced Inorganic Chem. 2nd ed (1966) pp. 920-923.

Primary Examiner—Alan Siegel
Attorney, Agent, or Firm—Herbert M. Wolfson; James E. Shipley

[57]    ABSTRACT

Process for the preparation of fluorinated alkanes by contacting a starting material of halogenated alkene or alkane with 1 to 150 molar equivalents based on catalyst of HF, 1 to 30 molar equivalents based on catalyst of a dehydrating agent and less than 100 molar equivalents based on catalyst of a starting material, the catalyst being selected from niobium oxide or tantalum oxide, at a temperature of 0° C. to 185° C. The preferred dehydrating agent is a combination of chlorosulfonic acid and thionyl chloride.

12 Claims, No Drawings

FLUORINATION PROCESS

This is a continuation of application Ser. No. 07/810,525 filed Dec. 18, 1991, now abandoned, which is a continuation of application Ser. No. 07/532,617 filed Jun. 4, 1990, now abandoned.

FIELD OF THE INVENTION

This invention relates to a process for the preparation of fluorinated alkanes by contacting halogenated alkenes or alkanes with hydrogen fluoride (HF) in the presence of niobium pentoxide ($Nb_2O_5$) or tantalum pentoxide ($Ta_2O_5$) and chlorosulfonic acid ($HOSO_2Cl$) and thionyl chloride ($SOCl_2$).

BACKGROUND OF INVENTION

A. E. Feiring, Journal of Fluorine Chemistry, 13, 7–18 (1979) discloses the use of tantalum pentafluoride as a catalyst for the addition of hydrogen fluoride to tetra- and trichloroethane and related compounds. The catalyst is also useful in fluorine-chlorine exchange reactions. However, under the conditions of the batch experiments [$HF/CCl_2=CCl_2=2.5$, temperature = 150° C., reaction time = six hours] catalysts such as $BF_3$, $TaCl_5$, $Ta_2O_5$, $CoF_3$, $V_2O_5$, $ZrCl_4$, $NbCl_5$, $HgO$, and $WCl_6$ showed no catalytic activity for the addition of HF to tetrachloroethylene.

The use of tantalum pentafluoride as a catalyst for the addition of hydrogen fluoride to unsaturated compounds has been disclosed and claimed by Feiring in U.S. Pat. No. 4,258,255.

The use of dehydrating agents to prepare anhydrous $TaF_5$ has been disclosed and claimed in Kim U.S. Pat. No. 4,124,692.

The need to provide an economically attractive process to produce highly fluorinated, hydrogen-containing alkanes useful as alternatives to current products for refrigerants, blowing agents, etc. has sparked interest in this area.

This invention provides a low cost process for the preparation of fluorinated alkanes made by catalyzed HF addition to olefins and/or fluorine for chlorine exchange on chlorinated alkanes using a system comprised of $Ta_2O_5$ or $Nb_2O_5$, a dehydrating agent(s), e.g., $HOSO_2Cl$ (chlorosulfonic acid), and $SOCl_2$ (thionyl chloride) and excess HF.

SUMMARY OF THE INVENTION

The process of this invention comprises contacting at a temperature from about 0° C. to about 185° C. a starting material selected from halogenated alkenes or halogenated alkanes of the following formulas

wherein $R_1$, $R_2$, $R_3$, $R_4$, $R_5$, $R_6$, $R_7$ and $R_8$ are H, F, Cl, Br, or $C_xZ_{2x+1}$, wherein Z is H, F, Cl or Br, x is an integer from 1–10, and wherein at least one of $R_1$–$R_4$ and $R_5$–$R_8$ is Br or Cl or a bromine or chlorine-substituted group, with HF and at least one dehydrating agent, in the presence of at least one catalyst selected from $Nb_2O_5$ and $Ta_2O_5$, to produce reaction products, the mole ratio of HF to Ta or Nb being from 1 to 150, the mole ratio of the dehydrating agent to Ta or Nb being from 1 to 30, and the mole ratio of the starting material to Ta or Nb being less than 100; and removing the reaction products from contact with the catalyst and isolating a fluorinated alkane having at least one more fluorine atom than the starting material.

The preferred process of this invention comprises contacting at a temperature from about 0° C. to about 185° C. a starting material selected from halogenated alkenes or halogenated alkanes of the following formulas

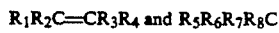

wherein $R_1$, $R_2$, $R_3$, $R_4$, $R_5$, $R_6$, $R_7$ and $R_8$ are H, F, Cl, Br, or $C_xZ_{2x+1}$, wherein Z is H, F, Cl or Br x is an integer from 1–10, and wherein at least one of $R_1$–$R_4$ and $R_5$–$R_8$ is Br or Cl or a bromine or chlorine-substituted group, with HF, $HOSO_2Cl$ and $SOCl_2$, in the presence of at least one catalyst selected from $Nb_2O_5$ and $Ta_2O_5$, to produce reaction products, the mole ratio of HF to Ta or Nb being from 1 to 150, the mole ratio of $HOSO_2Cl$ to Ta or Nb being from 1 to 30, and the mole ratio of $SOCl_2$ to Ta or Nb being from 0.5 to 20; and the mole ratio of the starting material to Ta or Nb being less than 100; and removing the reaction products from contact with the catalyst and isolating a fluorinated alkane having at least one more fluorine atom than the starting material.

DETAILS OF THE INVENTION

The fluorinated alkane produced in accordance with the instant invention has at least one more, and preferably two or more fluorine atoms than the halogenated alkene or alkane starting material and at least one of the fluorine atoms is the result of the halogen exchange reaction. For example, when the starting halogenated alkene or alkane is $CCl_2=CCl_2$ or $Cl_3CHCl_2$, respectively, the more favored products will be $CF_3CHCl_2$ and $CF_2ClCHCl_2$, and when the starting halogenated alkene or alkane is $Cl_2C=CHCl$ or $CCl_3CH_2Cl$, respectively, the favored product is $CF_3CH_2Cl$. When the starting halogenated alkene or alkane is $Cl_2C=CH_2$ or $Cl_3C-CH_3$, respectively, the product can be $CFCl_2CH_3$, $CF_2ClCH_3$, and $CF_3CH_3$, depending on process conditions.

To achieve the optimum degree of halogen exchange, the halogenated organic starting material is contacted with a metal oxide, preferably tantalum pentoxide or niobium pentoxide, and the mole ratio of halogenated alkane or alkene to Ta or Nb is less than 100. The catalyst, preferably tantalum pentoxide, is a commercially available and relatively inexpensive (compared for example to tantalum pentachloride or tantalum pentafluoride) crystalline solid and can be used alone or on a support such as carbon or fluorinated alumina. Other forms of oxides of niobium or tantalum can be used, such as $MO_2X(H_2O)_n$, $MOX_3(H_2O)_n$, $AMOX_5(H_2O)_n$, $AMO_2X_3(H_2O)_n$, where "A" is at least one divalent cation or two monovalent cations, "M" is Nb or Ta, "X" is F, Cl, or Br, and "n" is a number from 0 to 25.

In combination with the catalyst, it is preferred to use from greater than 1 to 150 molar equivalents of HF, based on the tantalum or niobium catalyst, preferably at least 10 to 140 molar equivalents, and, more preferably, at least 20 to 130 molar equivalents, to achieve optimum halogen exchange and consequent high yields of fluorinated alkanes.

In combination with the catalyst and HF, it is preferred to use 1 to 30 molar equivalents of $HOSO_2Cl$, based on tantalum or niobium, preferably 3 to 20 molar equivalents, and more preferably 5 to 18 molar equivalents, to achieve optimum halogen exchange and consequent high yields of fluorinated alkanes. It is also possible to use other equivalents of $HOSO_2Cl$, such as $HOSO_2F$, $HOSO_2CF_3$, $HOSO_2CH_3$, $SO_3$, $H_2SO_4/SO_3$, $H_2SO_4$, or any other $SO_3$ equivalent or carrier.

In combination with the catalyst, HF, and $HOSO_2Cl$ or equivalent thereof, it is preferred to utilize 0.5 to 20 molar equivalents of $SOCl_2$, based on the starting alkene or alkane, preferably 0.75 to 10 molar equivalents, and more preferably 1 to 6 molar equivalents, to achieve optimum halogen exchange and consequent high yields of fluorinated alkanes. It is also possible to use other dehydrating agents of the general formula, $CYY'Y''(C=O)X$, wherein Y, Y' and Y'' are selected from H, F, Cl or Br and X is F, Cl or Br. Other possible dehydrating agents may be selected from $Cl(C=O)(C=O)Cl$, $POCl_3$, $PCl_5$, $PCl_3$, $SO_2Cl_2$, $BCl_3$, $SiCl_4$, $Cl(C=O)Cl$, $Cl(C=O)F$ and $F(C=O)F$.

A variety of alkenes and alkanes may be used as starting materials. Preferred halogenated alkenes are of the formula $R_1R_2C=CR_3R_4$, wherein $R_1$, $R_2$, $R_3$, $R_4$, are H, F, Cl, Br, or $C_xZ_{2x+1}$, wherein Z is selected from at least one of the group consisting of H, F, Cl, or Br and at least one of $R_1$, $R_2$, $R_3$ and $R_4$ are either Br or Cl or a bromine or chlorine-substituted group. Preferred alkanes are of the formula $R_5R_6R_7R_8C$, wherein $R_5$, $R_6$, $R_7$, are H, F, Cl, Br, or $C_xZ_{2x+1}$, wherein Z is selected from at least one of the group consisting of H, F, Cl, or Br and x equals 1 to 10 and wherein $R_8$ is Br or Cl. Specifically preferred halogenated alkenes and alkanes are $CCl_2=CCl_2$, $CHCl=CCl_2$, $CH_2=CCl_2$, cis- or trans-$CHCl=CHCl$, $CH_2=CHCl$, $CCl_3CHCl_2$, $CCl_3CH_2Cl$, $CH_2ClCH_2Cl$, $CHCl_2CHCl_2$, and $CCl_3CH_3$.

An advantage of the instant invention is that small amounts of water in the reactants may be removed by the combination of the drying agents, e.g., $SOCl_2$ and $HOSO_2Cl$. For example, water, which may be a product of the reaction of $Ta_2O_5$ and HF:

($Ta_2O_5$ and $10HF \rightarrow 2TaF_5 + 5H_2O$), would be removed by the drying agents during the process of the invention.

Another advantage of the instant invention is that precautions need not be taken when charging tantalum or niobium catalyst since the drying agents employed will remove adventitious water, waters of hydration, or water formed in the reaction of metal oxides with HF. It was unexpected that $Ta_2O_5$ operates as a catalyst since, in the absence of drying agents, $Ta_2O_5$ shows no catalytic activity with any of the starting alkenes or alkanes described herein. Prior art (U.S. Pat. No. 4,124,692) teaches that it is possible to make $TaF_5$ from fluorotantalic acids using dehydrating agents such as $CHX_3$, $CX_4$, $COX_2$, $CSX_2$, wherein X comprises Cl, Br, or mixtures thereof, but the dehydration does not go to completion for fluorotantalic acids having a high atom ratio of oxygen to tantalum (O/Ta=2.5), as is the case for $Ta_2O_5$. Moreover, it teaches that it is preferred that excess HF (i.e. the amount of excess of that required to convert the tantalum compounds to fluorotantalic acids) be removed prior to contact with the dehydrating agent since said agent(s) will react with the HF to form fluoro derivatives. Hence, it was a complete surprise that $Ta_2O_5$ operates as a catalyst, even when used with the proper ratio of dehydrating agent and chlorosulfonic acid.

HF, which is commercially available, can be used in the reaction directly. The halogenated alkenes and alkanes, and the drying agents contain little or no water and can similarly be used directly.

The reaction can be carried out in the liquid phase or vapor phase and at autogenous pressures or under constant pressure ranging from atmospheric to superatmospheric. Both the liquid phase and vapor phase processes include batch, semicontinuous, and continuous modes of operation.

The reaction is normally carried out at a temperature from 0° C. to 185° C., and preferably from 35° C. to 160° C.

Pressure is not critical. Atmospheric and autogenous pressures are the most convenient and are therefore preferred. Means can be provided for the venting of any excess pressure due to formation of hydrogen chloride in the substitution reaction and can offer the advantage in minimizing the formation of side products.

The reaction vessel is constructed from materials which are resistant to the action of HF and "superacid" systems. Examples include stainless steel, high nickel alloys such as monel, "Hastelloy" and "Inconel", plastics such as polytetrafluoroethylene, polychlorotrifluoroethylene, polyethylene, and polypropylene, and ceramic materials such as alpha-silicon carbide and aluminum nitride. The high nickel alloys are preferred because of the superacidities of pentavalent tantalum and pentavalent niobium systems in anhydrous HF.

The liquid phase reactions are conducted by introducing the tantalum or niobium oxide and the halogenated alkene or halogenated alkane, thionyl chloride, and chlorosulfonic acid in any order into the reaction vessel. Generally, the $Ta_2O_5$, the starting alkene or alkane, the $SOCl_2$, and the $HOSO_2Cl$ are placed in the reaction vessel in an inert atmosphere chamber. The reaction vessel is cooled, and the required amount of HF is condensed in the vessel. The vessel may be evacuated prior to the introduction of hydrogen fluoride. The contents of the vessel are raised to the appropriate reaction temperature and agitated by shaking or stirring for a length of time sufficient to cause the desired reaction to occur.

The products are isolated by any of a variety of well-known techniques such as distillation or drowning into ice, washing with aqueous caustic, then water.

Under the reaction conditions set forth above, a portion of the $Ta_2O_5$ or $Nb_2O_5$ may be in the form of $M(Cl)_m(F)_n(O)_o(SO_3Cl)_p(SO_3F)_q(SO_3H)_r$, where $m+n+p+q+2o+r$ is equal to 5, and M is Nb or Ta.

The fluorinated alkanes produced by the invention have utility as refrigerants, solvents blowing agents, cleaning agents, propellants, dielectric fluids, carriers for sterilant gases and fire extinguishants.

In the following illustrative Examples all parts are molar proportions and all temperatures are Centigrade unless otherwise stated. All reactions used commercial anhydrous HF and were carried out with the exclusion of water. The product mixtures were analyzed by gas chromatography (GC) and mass spectroscopy (MS) or GCMS to identify the individual products. Results are in GC area percent.

EXAMPLE 1

To a 150 cc stainless steel single ended cylinder in a drybox was added $Ta_2O_5$ (10.1 gm, 0.0229 mol), $HOSO_2Cl$ (47.2 gm, 0.405 mol), $SOCl_2$ (16.4 gm, 0.138 mol), and $CCl_2=CCl_2$ (11.2 grams, 0.0675 mol). HF (20.4 gm, 1.04 mol) was added by vacuum-line distillation. The cylinder was then fitted with a reflux condenser operating at 10° C., a pressure gauge and a back pressure regulator set at 500 psi. The cylinder containing the reactants was immersed in an oil bath set at 158° C. and the reaction temperature, monitored by a thermocouple inside of the cylinder, was kept at 148°–152° C. for two hours while the autogenous pressure exceeded of 500 psi. Organic products were isolated by vacuum transfer of the contents of the reaction cylinder at the end of the run to a transfer cylinder containing a dip leg. The contents of the transfer cylinder were then transferred onto ice using nitrogen gas; 4.8 grams of organic were isolated and analyzed as follows: $CHCl_2CFCl_2$ (0.9%), $CHCl_2CF_2Cl$ (94.9%), and $CHCl_2CF_3$ (1.4%) with trace amounts of other organics.

EXAMPLE 2

To a 150 cc stainless steel single ended cylinder in a drybox was added $Ta_2O_5$ (8.1 gm, 0.0183 mol), $HOSO_2Cl$ (37.7 gm, 0.324 mol), $SOCl_2$ (13.1 gm, 0.110 mol), and perclene (8.9 grams, 0.0537 mol). HF (20.4 gm, 1.04 mol) was added by vacuum-line distillation. The cylinder was then fitted with a reflux condenser operating at 10° C., a pressure gauge and a back pressure regulator set at 500 psi. The cylinder containing the reactants was immersed in an oil bath set at 158° C. and the reaction temperature, monitored by a thermocouple inside of the cylinder, was kept at 148°–152° C. for two hours while generating an autogenous pressure in excess of 500 psi. Organic products were isolated by vacuum transfer of the contents of the reaction cylinder at the end of the run to a transfer cylinder containing a dip leg. The contents of the transfer cylinder were then transferred onto ice using nitrogen gas; 3.78 grams of organic were isolated and analyzed as follows: $CHCl_2CFCl_2$ (1.5%), $CHCl_2CClF_2$ (94%), and $CHCl_2CF_3$ (0.6%) with trace amounts of other organics.

CONTROL EXAMPLE 2A

The following is a comparison using $TaF_5$. To a 150 cc stainless steel single ended cylinder in a drybox was added $TaF_5$ (5.6 gm, 0.0203 mol), $HOSO_2Cl$ (41.6 gm, 0.357 mol), $SOCl_2$ (14.4 gm, 0.121 mol), and perclene (8.9 grams, 0.0597). HF (22.5 gm, 1.125 mol) was added by vacuum distillation. The cylinder was then fitted with a reflux condenser operating at 10° C., a pressure gauge and a back pressure regulator set at 500 psi. The cylinder containing the reactants was immersed in an oil bath set at 158° C. and the reaction temperature, monitored by a thermocouple inside of the cylinder, was kept at 141°–146° C. for 2.5 hours while generating an autogenous pressure in excess of 500 psi. Organic products were isolated by vacuum transfer of the contents of the reaction cylinder at the end of the run to a transfer cylinder containing a dip leg. The contents of the transfer cylinder were then transferred onto ice using nitrogen gas; 5.50 grams of organic were isolated and analyzed as follows: $CHCl_2CCl_2F$ (0.4%), $CHCl_2CClF_2$ (96%), and $CHCl_2CF_3$ (2.3%), showing that $Ta_2O_5$ (when used according to this invention) and $TaF_5$ display similar catalytic activity.

EXAMPLE 3

To a 150 cc stainless steel single ended cylinder in a drybox was added $Ta_2O_5$ (8.1 gm, 0.0183 mol), $SOCl_2$ (13.1 gm, 0.110 mol), and perclene (8.9 grams, 0.0538 mol). HF (22.5 gm, 1.125 mol) was added by vacuum distillation. The cylinder was then fitted with a reflux condenser operating at 0° C., a pressure gauge and a back pressure regulator set at 500 psi. The cylinder containing the reactants was immersed in an oil bath set at 158° C. and the reaction temperature, monitored by a thermocouple inside of the cylinder, was kept at 132°–137° C. for 2.0 hours while generating an autogenous pressure not exceeding 470 psi. Organic products were isolated by vacuum transfer of the contents of the reaction cylinder at the end of the run to a transfer cylinder containing a dip leg. The contents of the transfer cylinder were then transferred onto ice using nitrogen gas; 5.37 grams of organic were isolated and analyzed as follows: $CCl_2=CCl_2$ (87.1%) and $CHCl_2CCl_2F$ (8.5%) with trace amounts of other organics.

The preceding example demonstrates that $SOCl_2$ will operate as the sole dehydrating agent but that it is preferred to include $HOSO_2Cl$ in the dehydrating agent.

EXAMPLE 4

To a 150 cc stainless steel single ended cylinder in a drybox was added $Ta_2O_5$ (5.7 gm, 0.0129 mol), $HOSO_2Cl$ (26.7 gm, 0.229 mol), and perclene (6.3 grams, 0.040 mol). HF (21.4 gm, 1.07 mol) was added by vacuum distillation. The cylinder was then fitted with a reflux condenser operating at 0° C., a pressure gauge and a back pressure regulator set at 500 psi. The cylinder containing the reactants was immersed in an oil bath set at 160° C. and the reaction temperature, monitored by a thermocouple inside of the cylinder, was kept at 147°–154° C. for 2.25 hours while generating an autogenous pressure not exceeding 470 psi. Organic products were isolated by vacuum transfer of the contents of the reaction cylinder at the end of the run to a transfer cylinder containing a dip leg. The contents of the transfer cylinder were then transferred onto ice using nitrogen gas; organic was isolated and analyzed as follows: $CCl_2=CCl_2$ (49.3%), $CHCl_2CCl_2F$ (36.5%), $CHCl_2CClF_2$ (7.9%), $CHCl_2CCl_3$ (1.6%) with trace amounts of other organics.

The preceding example demonstrates that $HOSO_2Cl$ alone will operate but that it is preferred to include $SOCl_2$ along with $HOSO_2Cl$ as the dehydrating agent.

EXAMPLE 5

To a 400 cc "Hastelloy" C single ended agitated bomb was added $Nb_2O_5$ (12.0 gm, 0.045 mol), $HOSO_2Cl$ (69.9 gm, 0.600 mol), $SOCl_2$ (19.6 gm, 0.165 mol), and $CHCl=CCl_2$ (197 grams, 1.50 mol). HF (230 gm, 11.5 mol) was added by vacuum distillation. The vessel was heated to 85° C. for two hours; autogenous pressure developed in excess of 2000 psi. At the end of this period, the bomb was cooled to 0° C. and vented through a caustic scrubber. The contents were then poured onto ice and the organic products isolated and analyzed as follows: $CH_2ClCFCl_2$ (90%), $CHCl=CCl_2$ (6.7%), and $CH_2ClCCl_3$ (2.4%) with trace amounts of other organics.

What is claimed:

1. A process for preparing fluorinated alkanes which comprises contacting, at a temperature of 0° C. to 185° C. under substantially anhydrous conditions, a starting material selected from halogenated alkanes and halogenated alkenes of the following formulas

wherein

R$_1$, R$_2$, R$_3$, R$_4$, R$_5$, R$_6$, R$_7$ and R$_8$ are H, F, Cl, Br, or C$_x$Z$_{2x+1}$, wherein Z is H, F, Cl or Br x is an integer from 1-10, and wherein at least one of R$_1$-R$_4$ and R$_5$-R$_8$ is Br or Cl or a bromine or chlorine-substituted group, with HF, HOSO$_2$Cl and SOCl$_2$, in the presence of at least one catalyst selected from Nb$_2$O$_5$ and Ta$_2$O$_5$, to produce reaction products, the mole ratio of HF to Ta or Nb being from 1 to 150, the mole ratio of HOSO$_2$Cl to Ta or Nb being from 1 to 30, and the mole ratio of SOCl$_2$ to Ta or Nb being from 0.5 to 20; and the mole ratio of the starting material to Ta or Nb being less than 100; and removing the reaction products from contact with the catalyst and isolating a fluorinated alkane having at least one more fluorine atom than the starting material.

2. The process of claim 1 wherein the amount of HF, based on the Ta or Nb is 20 to 130 molar equivalents.

3. The process of claim 1 wherein the catalyst is Ta$_2$O$_5$.

4. The process of claim 1 wherein the temperature is 35° C. to 160° C.

5. The process of claim 1 wherein the amount of HOSO$_2$Cl is 5 to 18 molar equivalents based on the Ta or Nb.

6. The process of claim 1 wherein the amount of SOCl$_2$ is 1 to 6 molar equivalents based on the Ta or Nb.

7. The process of claim 1 wherein the starting material is at least one halogenated alkene selected from the following compounds:

CCl$_2$=CCl$_2$, CHCl=CCl$_2$, CH$_2$=CCl$_2$, cis- and trans-CHCl=CHCl and CH$_2$=ChCl.

8. The process of claim 1 wherein the starting material is at least one halogenated alkane selected from the following compounds:

CCl$_3$CHCl$_2$, CCl$_3$CH$_2$Cl, CH$_2$ClCH$_2$Cl, CHCl$_2$CHCl$_2$ and CCl$_3$CH$_3$.

9. A process for preparing fluorinated alkanes which comprises contacting, at a temperature of 0° C. to 185° C. under substantially anhydrous conditions, a starting material selected from halogenated alkanes and halogenated alkenes of the following formulas:

R$_1$R$_2$C=CR$_3$R$_4$ and R$_5$R$_6$R$_7$R$_8$C wherein

R$_1$, R$_2$, R$_3$, R$_4$, R$_5$, R$_6$, R$_7$ and R$_8$ are H, F, Cl, Br, or C$_x$Z$_{2x+1}$, wherein Z is H, F, Cl or Br x is an integer from 1-10, and wherein at least one of R$_1$-R$_4$ and R$_5$-R$_8$ is Br or Cl or a bromine or chlorine-substituted group, with HF and a compound selected from the group consisting of HOSO$_2$Cl, HOSO$_2$F, HOSO$_2$CF$_3$, HOSO$_2$CH$_3$, SO$_3$, H$_2$SO$_4$/SO$_3$, and H$_2$SO$_4$ and SOCl$_2$, in the presence of at least one catalyst selected from Nb$_2$O$_5$ and Ta$_2$O$_5$, to produce reaction products, the mole ratio of HF to Ta or Nb being from 1 to 150, the mole ratio of HOSO$_2$Cl, HOSO$_2$F, HOSO$_2$CF$_3$, HOSO$_2$CH$_3$, SO$_3$, H$_2$SO$_4$/SO$_3$, or H$_2$SO$_4$ to Ta or Nb being from 1 to 30, and the mole ratio of SOCl$_2$ to Ta or Nb being from 0.5 to 20; and the mole ratio of the starting material to Ta or Nb being less than 100; and removing the reaction products from contact with the catalyst and isolating a fluorinated alkane having at least one more fluorine atom than the starting material.

10. A process for preparing fluorinated alkanes which comprises contacting, at a temperature of 0° C. to 185° C. under substantially anhydrous conditions, a starting material selected from halogenated alkanes and halogenated alkenes of the following formulas:

R$_1$R$_2$C=CR$_3$R$_4$ and R$_5$R$_6$R$_7$R$_8$C wherein

R$_1$, R$_2$, R$_3$, R$_4$, R$_5$, R$_6$, R$_7$ and R$_8$ are H, F, Cl, Br, or C$_x$Z$_{2x+1}$, wherein Z is H, F, Cl or Br x is an integer from 1-10, and wherein at least one of R$_1$-R$_4$ and R$_5$-R$_8$ is Br or Cl or a bromine or chlorine-substituted group, with HF, and at least one compound selected from HOSO$_2$Cl and SOCl$_2$, in the presence of at least one catalyst selected from Nb$_2$O$_5$ and Ta$_2$O$_5$, to produce reaction products, the mole ratio of HF to Ta or Nb being from 1 to 150, the mole ratio of HOSO$_2$Cl to Ta or Nb being from 1 to 30, and the mole ratio of SOCl$_2$ to Ta or Nb being from 0.5 to 20; and the mole ratio of the starting material to Ta or Nb being less than 100; and removing the reaction products from contact with the catalyst and isolated a fluorinated alkane having at least one more fluorine atom than the starting material.

11. The process of claim 10 wherein said compound is HOSO$_2$Cl.

12. The process of claim 10 wherein said compound is SOCl$_2$.

* * * * *